United States Patent [19]

Roberts

[11] 4,173,703

[45] Nov. 6, 1979

[54] PREPARATION OF CARBAMATES

[75] Inventor: Floyd E. Roberts, Princeton, N.J.

[73] Assignee: Merck & Co., Inc., Rahway, N.J.

[21] Appl. No.: 881,201

[22] Filed: Feb. 27, 1978

Related U.S. Application Data

[60] Division of Ser. No. 747,839, Dec. 6, 1976, which is a continuation of Ser. No. 398,495, Nov. 18, 1973, abandoned, which is a continuation of Ser. No. 207,982, Dec. 14, 1971, abandoned.

[51] Int. Cl.$^2$ ............................................. C07D 501/20
[52] U.S. Cl. ...................................... 544/16; 544/21; 424/246
[58] Field of Search ........................................... 544/16

[56] References Cited

U.S. PATENT DOCUMENTS

| | | | |
|---|---|---|---|
| 3,770,590 | 11/1973 | Anamine et al. | 544/16 |
| 3,801,464 | 4/1974 | Gorman et al. | 544/16 |
| 3,905,963 | 9/1975 | Webber | 544/16 |

*Primary Examiner*—Nicholas S. Rizzo
*Attorney, Agent, or Firm*—James A. Arno; Julian S. Levitt

[57] ABSTRACT

Alcohols are reacted with silylated isocyanate compounds to produce the N-substituted carbamoyloxy derivatives which are cleaved to obtain the carbamate.

3 Claims, No Drawings

PREPARATION OF CARBAMATES

This is a division of application Ser. No. 747,839, filed Dec. 6, 1976 which is a continuation of U.S. patent application Ser. No. 398,495 filed Nov. 18, 1973, now abandoned, which in turn is a continuation of U.S. patent application Ser. No. 207,982 filed Dec. 14, 1971, now abandoned.

This invention relates to the preparation of carbamates and products useful in their preparation. More particularly, it is concerned with a method of converting alcohols to the corresponding carbamoyloxy derivatives, reagents suitable for this conversion, and with intermediate substituted carbamoyloxy compounds useful in their preparation.

The carbamates are valuable derivatives of alcohols which are useful in their identification and characterization. In addition, carbamates such as meprobamate, carbachol, and novobiocin have been found to be useful medicinal products. More recently it has been found that 3-carbamoyloxymethyl cephalosporins obtained by fermentation are valuable antibiotic substances. The process of the present invention is particularly valuable in providing a method suitable for the preparation of such cephalosporins as well as other carbamates.

In accordance with one embodiment of this invention, it is now found that alcohols can be converted to the corresponding carbamoyloxy compounds by reacting the alcohol with triorganosilyl isocyanate and then replacing the labile triorganosilyl group with hydrogen. This process can be illustrated as follows:

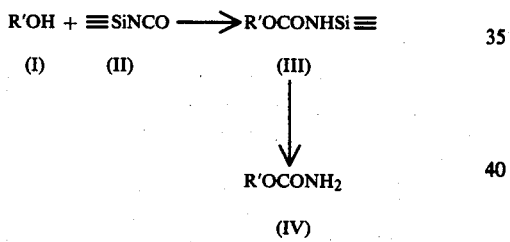

The group represented by $Si\equiv$ is a triorganosilyl group which is readily cleaved and replaced by hydrogen. Although various triorganosilyl isocyanates can be used, it is preferred to use N-trimethylsilyl isocyanate since this product is most readily available.

In this process the alcohol (I), wherein R' represents the organic radical of the alcohol, is reacted with the silyl isocyanate (II) to produce the N-substituted intermediate product (III), which is hydrolyzed to produce the desired carbamate (IV).

The first step of the above-described process, namely, the preparation of the intermediate imidodicarboxylates or the N-triorganosilyl carbamoyloxy compound (III) is carried out by intimately contacting the alcohol with the isocyanate, preferably in a non-protic solvent such as methylene chloride, tetrahydrofuran, dimethylformamide, and the like. In general, we prefer to carry out the reaction under anhydrous conditions and to have at least an equimolar quantity of the isocyanate present in order to obtain maximum yields of the desired intermediate product. In general, the reaction can be carried out at temperatures between about 0° C. and 30° C. However, it is generally preferred to carry out the reaction at about room temperature. The precise conditions for carrying out this process will depend in part upon the particular alcohol which is being reacted. The removal of the protecting group and its replacement by hydrogen is readily carried out by hydrolysis under slightly acidic conditions.

The process of this invention is particularly valuable for producing cephalosporin compounds having a 3-carbamoyloxymethyl substituent. This embodiment of our invention can be represented as follows:

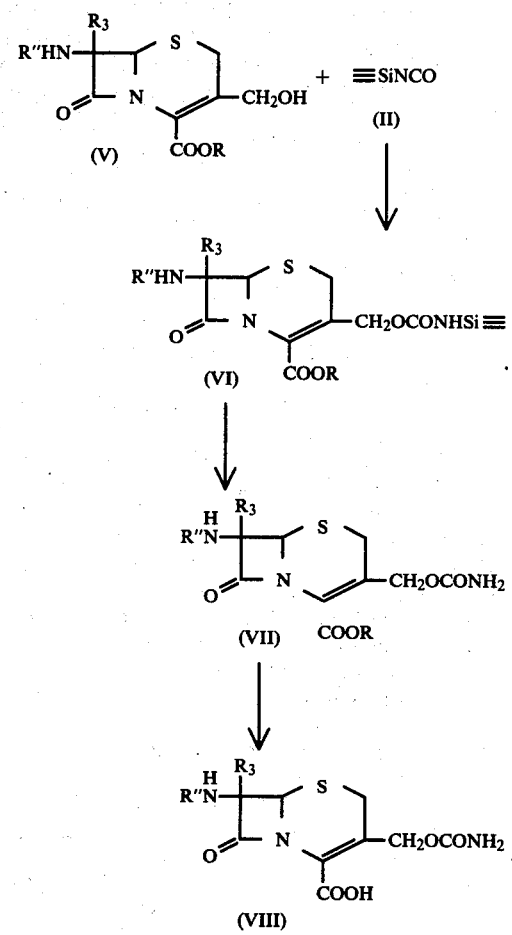

wherein $Si\equiv$ is as defined above, R" represents an acyl radical, $R_3$ represents hydrogen or a group such as methoxy, and R represents hydrogen or a blocking substituent. In this process the 3-hydroxymethyl cephalosporin compound (V) is reacted with the isocyanate (II) to produce the intermediate N-substituted carbamoyloxy compound (VI) which is then deblocked to produce the 3-carbamoyloxymethyl ester (VII). The carboxy blocking substituent is then removed to afford the free acid (VIII). The acyl radical represented by R" can be an acyl group of a carboxylic acid or a substituted sulfonyl radical such as phenylsulfonyl, ethylsulfonyl, benzylsulfonyl, 2,5-dimethylphenylsulfonyl, 4-chlorophenylsulfonyl, 4-methoxyphenylsulfonyl, and the like. Thus, R" can be an aliphatic, aromatic or heterocyclic, araliphatic or heterocyclylaliphatic carboxylic acid radical such as the acyl radical of the known cephalosporins and penicillins. The acyl substituents of the general formula $R_{11}R_{10}CHCO$ wherein $R_{10}$ and $R_{11}$ are as defined below represent a preferred group of substituents because of their generally useful antibiotic activity. $R_{10}$ represents hydrogen, halo, amino, guanidino, phosphone, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxamidomethyl, aminomethyl, nitro, methoxy or methyl. Examples of these preferred substituents that might be mentioned are phenacetyl, 3-bromphenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

Particularly preferred 3-hydroxymethylcephalosporin compounds which can be converted to the corresponding 3-carbamoyloxymethyl cephalosporin compounds in accordance with this invention are those wherein $R_{10}$ is hydrogen, amino, or carboxy and $R_{11}$ is phenyl or a 5-membered heterocyclic ring having one oxygen or one sulfur hetero atom, and especially those wherein R" is benzylcarbonyl, 2- and 3-thienylmethylcarbonyl or 2- and 3-furylmethylcarbonyl.

The cephalosporin carbamates are prepared by reacting cephalosporin compounds having a 3-hydroxymethyl substituent, or a salt or ester of such cephalosporins, with the isocyanate and then cleaving the resulting reaction product as described above. If the cephalosporin being reacted contains other substituents which react with the isocyanate, such as other hydroxy groups or amino groups, these substituents are blocked or protected by groups such as trityl, tertiary butyloxycarbonyl, N-trichloroethoxycarbonyl, and the like, and then removed after the carbamoyloxy group is introduced. For example, 7-tritylaminocephalosporanic acid is intimately contacted with citrus acetylesterase to produce 7-tritylaminodesacetylcephalosporanic acid which, on reaction with the isocyanate and hydrolysis of the reaction product, affords the 3-carbamoyloxymethyl compound. Removal of the protective trityl group by methods known in the art affords 3-carbamoyloxymethyl-7-aminodesacetylcephalosporanic acid which can be acylated by known methods to produce 3-carbamoyloxymethyldesacetyl cephalosporins.

Alternatively, 3-hydroxymethyl-7-acylamido-3-cephem-4-carboxylic acid and the corresponding compounds having a substituent at the 7-position, such as methoxy, in place of hydrogen, can be converted to the corresponding 3-carbamoyloxymethyl cephalosporin compounds by the process of this invention.

The 3-carbamoyloxymethyl cephalosporins prepared in accordance with the process of this invention are valuable antibiotics which are active at low levels against various gram-positive and gram-negative pathogens such as *Staphylococcus aureus, Staphylococcus pyogenes, Proteus vulgaris, Escherichia coli* and the like. These new cephalosporins are therefore useful in treating infections in humans and animals. They can also be used in dilute aqueous concentrations containing less than 100 parts of antibiotic per million parts of solution in removing susceptible organisms from pharmaceutical, medical and dental equipment, and for isolating microorganisms from mixtures of microorganisms.

In carrying out the above-described process, the carboxy group of the cephalosporin compound is blocked or protected by forming a suitable derivative which can be readily cleaved without affecting the β-lactam ring. Generally, it is preferred to block the carboxy substituent by forming a suitable ester. Examples of such esters that might me mentioned are the benzyl, benzhydryl, methoxymethyl, p-nitrophenyl, trimethylsilyl, trichloroethoxy, p-methoxybenzyl, phthalimidomethyl, and succinimidomethyl esters. These esters can be cleaved in accordance with methods known in the art to afford the free acid.

The following examples are provided to illustrate the above-described processes of the present invention.

EXAMPLE 1

3-Carbamoyloxymethyl-7-methoxy-7β-(2-thienylacetamido)-3-cephem-4-carboxylic acid To 10 ml. of a methylene chloride solution containing 650 mg. of benzhydryl 3-hydroxymethyl-7-methoxy-7β-(2-thienylacetamido)-3-cephem-4-carboxylate is added dropwise 115 mg. of N-trimethylsilyl isocyanate. The resulting reaction mixture is stirred at room temperature for 1 hour and then quenched onto ice and acidified to pH 5 with dilute HCl. The layers are separated and the organic phase is separated and dried over magnesium sulfate. Removal of the solvent under reduced pressure affords benzhydryl 3-carbamoyloxymethyl-7-methoxy-7β-(2-thienylacetamido)-3-cephem-4-carboxylate.

A cold solution of the benzhydryl ester of 3-carbamoyloxymethyl-7-methoxy-7β-(2-thienylacetamido)-3-cephem-4-carboxylic acid (136 mg.) in 1.1 ml. of anisole is stirred with 0.55 ml. of trifluoroacetic acid at 0° C. for ½ hour. The volatiles are removed in high vacuum, and the product is recrystallized from ethyl acetate. m.p. 165°-167° C.

Following the above-described procedures, benzhydryl 3-hydroxymethyl-7-methoxy-7β-acetamido-3-cephem-4-carboxylate and benzhydryl 3-hydroxymethyl-7-methoxy-7β-(2-furylacetamido)-3-cephem-4-carboxylate are converted to 3-carbamoyloxymethyl-7-methoxy-7β-acetamido-3-cephem-4-carboxylic acid and 3-carbamoyloxymethyl-7-methoxy-7β-(2-furylacetamido)-3-cephem-4-carboxylic acid (m.p. 156°-161° C.), respectively.

The starting materials in the foregoing example are prepared by incubating the benzhydryl esters of 7-methoxy-7β-(2-thienylacetamido), acetamido, or (2-furylacetamido) cephalosporanate with citrus acetylesterase in accordance with procedures well known in this art.

The benzhydryl esters of 7-methoxy-7β-(2-thienylacetamido)cephalosporanic acid, 7-methoxy-7β-acetamidocephalosporanic acid and 7-methoxy-7β-(2-furylacetamido)cephalosporanic acid are prepared as described in the pending U.S. application of Burton G. Christensen et al. Ser. No. 149,364 filed June 2, 1971.

EXAMPLE 2

3-Carbamoyloxymethyl-7β-(2-thienylacetamido)-3-cephem-4-carboxylic acid

Following the procedures in Example 1, an equivalent amount of methoxymethyl 3-hydroxymethyl-7β-(2-thienylacetamido)-3-cephem-4-carboxylic acid is reacted with N-trimethylsilyl isocyanate to obtain methoxymethyl 3-carbamoyloxymethyl-7β-(2-thienylacetamido)-3-cephem-4-carboxylate.

A suspension of the methoxymethyl ester (920 mg.) in 9.2 ml. of methanol containing 10% concentration HCl is stirred at room temperature for 90 minutes. A cold solution of 1.65 g. of sodium bicarbonate in 40 ml. of water is then added, and the clear solution concentrated to a volume of 30–35 ml. at room temperature under reduced pressure. The aqueous solution is then extracted with ethyl acetate and the organic layer discarded. The aqueous layer is cooled to 0°–5° C., covered with ethylacetate (40 ml.), and the pH adjusted to 1.8 with cold 10% HCl with stirring. The layers are separated and the ethyl acetate layer washed with ice water. The aqueous layer and the washing are combined and re-extracted with 2×20 ml. of ethyl acetate. The second ethyl acetate extract is washed twice with cold water and then combined with the first extract. The solvent is evaporated to dryness and dried to constant weight to afford 3-carbamoyloxymethyl-7β-(2-thienylacetamido)-3-cephem-4-carboxylic acid.

The starting material in this example is prepared by incubating the methoxymethyl ester of 7β-(2-thienylacetamido)cephalosporanic acid with citrus acetylesterase in accordance with procedures well known in this art. The methoxymethyl ester is prepared by esterifying the di(cyclohexyl)amine salt of 7β-(2-thienylacetamido)cephalosporanic acid with chloromethyl methylether in anhydrous methylene chloride solution which, upon evaporation of the solvent, affords the desired product.

The process of the present invention is also effected using the free acid or a salt thereof in place of the ester of the cephalosporin compound. However, usually it is preferred to use the ester since maximum yields of the desired product are obtained under optimum conditions.

We claim:

1. A compound of the formula

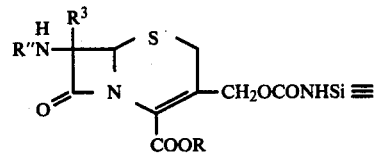

wherein R" represents an acyl group conventionally known in the cephalosporin art, $R_3$ represents hydrogen or methoxy, R represents hydrogen or a blocking group and Si≡ represents trimethylsilyl.

2. The compound of claim 1 wherein R" is 2-thienylacetamido and $R_3$ is hydrogen.

3. The compound of claim 1 wherein R" is 2-thienylacetamido and $R_3$ is methoxy.

* * * * *